(12) United States Patent
Gorges et al.

(10) Patent No.: US 10,874,371 B2
(45) Date of Patent: Dec. 29, 2020

(54) METHOD AND SYSTEM FOR ONLINE CALIBRATION OF A MEDICAL X-RAY DEVICE

(71) Applicant: THALES, Courbevoie (FR)

(72) Inventors: Sébastien Gorges, Saint Jean de Moirans (FR); Guillaume Bernard, Moirans (FR)

(73) Assignee: THALES, Courbevoie (FR)

( * ) Notice: Subject to any disclaimer, the term of this patent is extended or adjusted under 35 U.S.C. 154(b) by 190 days.

(21) Appl. No.: 16/031,943

(22) Filed: Jul. 10, 2018

(65) Prior Publication Data

US 2019/0015067 A1 Jan. 17, 2019

(30) Foreign Application Priority Data

Jul. 11, 2017 (FR) ...................................... 17 00740

(51) Int. Cl.
*A61B 6/00* (2006.01)
*A61B 90/00* (2016.01)
(52) U.S. Cl.
CPC ............ *A61B 6/581* (2013.01); *A61B 6/4405* (2013.01); *A61B 6/4441* (2013.01);
(Continued)
(58) Field of Classification Search
CPC .......... A61B 2090/3764; A61B 6/4405; A61B 6/4441; A61B 6/5205; A61B 6/5258;
(Continued)

(56) References Cited

U.S. PATENT DOCUMENTS

2006/0122495 A1* 6/2006 Kienzle, III ............. A61B 6/02
600/424
2008/0130827 A1 6/2008 Klingenbeck-Regn
(Continued)

FOREIGN PATENT DOCUMENTS

EP 3 141 187 A1 3/2017

OTHER PUBLICATIONS

Grzeda, et al., "C-arm rotation encoding with accelerometer", International Journal of Computer Assisted Radiology and Surgery, 5(4), pp. 385-391, 2010.
(Continued)

*Primary Examiner* — Chih-Cheng Kao
(74) *Attorney, Agent, or Firm* — BakerHostetler

(57) ABSTRACT

A method for calibrating a device D includes at least one radiation source and a detector, the radiation source and the detector being installed on at least one moving support, comprising at least the following elements: at least one first sensor positioned close to the radiation source and at least one second sensor positioned close to the detector, the two first and second sensors being configured to estimate through calculation a position Ps of the source and a position Pd of the detector, and a sensor for sensing the angular position of the moving support, a synchronization module configured to synchronously trigger the measurements of the sensors, a module for pre-processing the measurements of the sensors, the processing module comprising an input receiving an operating model M of the device and a data merging algorithm taking into account at least the two measurements of the sensors and the model M in order to estimate an accurate position value for the source Ps and for the detector Pd.

15 Claims, 2 Drawing Sheets

(52) U.S. Cl.
CPC ............ *A61B 6/5258* (2013.01); *A61B 6/547* (2013.01); *A61B 6/582* (2013.01); *A61B 6/587* (2013.01); *A61B 6/5205* (2013.01); *A61B 2090/3764* (2016.02)

(58) Field of Classification Search
CPC ......... A61B 6/547; A61B 6/581; A61B 6/582; A61B 6/587
See application file for complete search history.

(56) References Cited

U.S. PATENT DOCUMENTS

| | | |
|---|---|---|
| 2012/0236999 A1 | 9/2012 | Altvater et al. |
| 2014/0010349 A1 | 1/2014 | De Godzinsky et al. |
| 2015/0209599 A1* | 7/2015 | Schlosser ............. A61B 6/4417 600/427 |
| 2016/0278732 A1* | 9/2016 | Amiri .................. A61B 6/4405 |
| 2018/0153498 A1* | 6/2018 | Flexman ................ A61B 6/547 |

OTHER PUBLICATIONS

Grzeda, et al., "C-arm rotation encoding with accelerometers", International Journal of Computer Assisted Radiology and Surgery, 5(4), pp. 385-391, 2010.

Amiri, et al., "A low-cost tracked C-arm (TC-arm) upgrade system for versatile quantitative intraoperative imaging", International Journal of Computer Assisted Radiology and Surgery, 9(4), pp. 695-711, 2014.

* cited by examiner

METHOD AND SYSTEM FOR ONLINE CALIBRATION OF A MEDICAL X-RAY DEVICE

CROSS-REFERENCE TO RELATED APPLICATIONS

This application claims priority to foreign French patent application No. FR 1700740, filed on Jul. 11, 2017, the disclosure of which is incorporated by reference in its entirety.

FIELD OF THE INVENTION

The invention relates notably to a method and to a system for online calibration of a medical X-ray device and more particularly to radiology systems used for surgery or interventional radiology, such as mobile surgical C-arms. It is used notably for online calibration of what are termed C-arm devices.

BACKGROUND

It is common to use a mobile interventional radiology system to perform surgical or interventional procedures. These systems, also called mobile C-arms (block amplifier or surgical C-arms), allow the surgeon to acquire X-ray images during the intervention and to monitor the position of the tools (catheter, needle, prosthesis, etc.) in real time in a way that is as non-invasive as possible. The majority of these systems make it possible to obtain two-dimensional images with a video image stream of up to thirty images per second. These systems generally comprise an X-ray source and an image detector installed at the two ends of a C-arm, between which there is positioned an object that it is desired to image. The images acquired by the detector are the result of a projection of the object into the plane of the detector.

The practitioner then uses these two-dimensional 2D images to perform, in real time, a mental reconstruction of the morphology of the patient, allowing him to position, in real time, the instrument that is used with respect to an operating zone. He also mentally reorients the complete scene (patient+surgical instruments) in space in order to accurately control his movement.

Sophisticated systems have emerged in recent times. They make it possible to acquire a 3D image of the surgical instrument during the intervention. The system performs a rotation about the patient for the purpose of obtaining a set of 2D images. These 2D images are then processed by an image reconstruction algorithm, allowing a 3D volume image to be obtained. The reconstruction algorithm needs to know the exact geometry of the C-arm, namely the position of the detector and of the X-ray tube with respect to the patient or to an object, for each 2D image that is utilized. Current systems provide for carrying out 'offline' calibration, using for example a 3D calibration chart to determine the projection matrices. This 'offline' calibration is performed during preventive maintenance phases that the system undergoes, for example every six months or every year.

Patent application EP3141187 relates to a calibration chart for geometrically calibrating an X-ray imaging device intended to generate three-dimensional images of an object through reconstruction based on two-dimensional projections of said object. The calibration chart comprises a volume support equipped with markers having a radiological absorbance that provides contrast with respect to the volume support, the markers being distributed in a three-dimensional pattern. The markers are distributed into subsets of markers that are distributed in respective substantially parallel straight lines such that sequences of cross-ratios are able to be constructed from the respective subsets of markers. Each sequence of cross-ratios comprises a single cross-ratio for each quadruplet of markers in which the markers are ordered in an order depending on the rank numbers of the respective markers along the straight line on which they are aligned, in a first predefined direction, said order being common to all of the cross-ratios.

One calibration technique known from the prior art uses for example markers positioned on a phantom that serve as reference points in space. With the position of the markers in space being known, it is possible to deduce the geometry of the acquisition for each projection by transforming a system of equations derived from the position of the markers on the projected images.

Systems known from the prior art assume that the rotational acquisition is repeatable enough for the geometry determined 'offline' to be applicable to images acquired in real time during the intervention. The mechanics of the systems therefore had to be improved in order to make the C-arm stable during the rotational acquisition of the 2D images (reduction in mechanical play, stiffer components, etc.). These systems are not widespread as their cost is high on account of the mechanical modifications that have to be made. Moreover, it is not easy for manufacturers of the C-arm device to implement these modifications.

Some solutions known from the prior art provide for carrying out calibration 'online' using a method based on sensors that are integrated directly into the device and without having to analyse images containing radio-opaque markers.

A first solution uses a simple three-axis inertial sensor positioned on the detector or on the ray source. Such a method is described in the document by Grzeda Victor et al, entitled 'C-arm rotation encoding with accelerometer', International Journal of Computer Assisted Radiology and Surgery, 2010, 5(4), pp: 385-391.

A second solution uses two six-axis inertial systems and two laser telemeters, such as for example in the document by Amiri Shahram, Wilson David R., entitled 'A low-cost tracked C-arm (TC-arm) upgrade system for versatile quantitative intraoperative imaging', International Journal of Computer Assisted Radiology and Surgery, 9(4), pp: 695-711, 2014.

In the case of use requiring very high accuracy, for example in the surgical field, these methods are not optimal. Specifically, the accuracy that is achieved is not compatible with the desired 3D reconstruction quality.

In the document by Grzeda Victor, the idea of positioning the detector and the X-ray source using a three-axis accelerometer, adopting the principles introduced by navigation, was abandoned in favour of the idea of estimating the angle of rotation at its axis of rotation (replacing a rotary encoder using an accelerometer) and of deducing, online, the positions of a system with a reproducible path that is calibrated beforehand.

With a device comprising two six-axis inertial systems and two laser telemeters, the abovementioned document by Amiri Sharham, the accuracy obtained is of the order of:

1.5 mm+/−1.2 mm accuracy for locating the isocentre of the system, 2.3 mm+/−1.1 mm accuracy for 2D-3D calibration, 4.4 mm+/−1.9 mm accuracy in locating markers in the reconstructed scene.

These accuracy values are well below the accuracy values required for accurate and meticulous applications, notably in surgical applications, or in other fields requiring accuracy, for example in the metrology of components at the end of manufacture.

SUMMARY OF THE INVENTION

The idea of the present invention relates to a calibration method and system for estimating the geometry of a device online, during operation. The calibration will take place during the rotational acquisition of the device, so as not to inhibit the procedures of handling the device and, in particular, so as not to require burdensome and restrictive calibrations a priori (offline). The invention is applicable notably in the field of surgical operations, and more broadly to clinical use that is non-restrictive and has a fast execution time.

In the description, the terms 'apparatus' and 'device' denote one and the same object.

The expression system 'geometry' denotes all nine intrinsic parameters (characterization of the X-ray source/detector pair) and extrinsic parameters (characterization of the geometry of patient//X-ray source/detector set).

The invention relates to a system for calibrating a device D comprising at least one radiation source and a detector, the radiation source and the detector being installed on at least one moving support, the moving support being linked to a base via at least one axis of rotation, characterized in that it comprises at least the following elements:
  at least one first sensor positioned close to the radiation source and at least one second sensor positioned close to the detector, the two first and second sensors being configured to estimate through calculation a position Ps of the source and a position Pd of the detector, and a sensor for measuring the angular position of the moving support,
  a synchronization module configured to synchronously trigger the measurements of the sensors,
  a module for pre-processing the measurements of the sensors, said processing module comprising an input receiving an operating model M of the device and a data merging algorithm taking into account at least the two measurements of the sensors and the model M in order to estimate an accurate position value for the source Ps and for the detector Pd.

The measurement sensors are for example inertial sensors.

According to one embodiment, said inertial sensors are distributed along the support between the radiation source and the detector.

The system may comprise at least three inertial sensors, two of the inertial sensors being positioned at each end of the moving support and the third sensor midway between the two ends.

The moving support is, for example, an arm equipped with an encoder configured to measure an angular position Pa of the movement of the arm.

The moving support may also be an arm including N encoders, with N degrees of freedom of the system greater than or equal to 1. The moving support may be a C-arm.

The data merging algorithm is a Kalman algorithm or an extended Kalman algorithm.

The invention also relates to a method for online calibration of a device comprising at least one radiation source and a detector that are associated with at least one moving support, characterized in that it comprises at least the following steps:
  simultaneously recording measurements performed by at least one sensor close to the radiation source and a sensor close to the detector and a sensor configured to measure the angular position of the moving support,
  transmitting these measurements, as well as an operating model M of the device D, to a module configured to merge data in order to estimate a position value Pd for the detector and Ps for the source, as well as a measurement error.

To merge the data, it is possible to use a Kalman filter or an extended Kalman filter.

The measurements are performed for example by way of inertial sensors.

According to one variant embodiment, measurements given by the sensors close to the source and to the end are merged with the measurement of N encoders, with N corresponding to the number of degrees of freedom of the system and N being greater than or equal to 1.

Use is made for example of an optoelectronic sensor for measuring mechanical deformations of the arm, or one or more Bragg gratings or interferometers for determining deformation of the moving support.

To measure the mechanical deformation of the support, a device chosen from the following list is used: one or more interferometers or laser telemeters, one or more RFID/ultrasound sensors.

BRIEF DESCRIPTION OF THE DRAWINGS

Other features and advantages of the present invention will become more clearly apparent on reading the description of exemplary embodiments alongside the figures, in which.

DETAILED DESCRIPTION

In order to aid understanding of the subject of the present invention, the following example is given by way of illustration for a C-arm device used in the surgical field. Without departing from the scope of the invention, the invention could be implemented in any device comprising at least one radiation source and a detector, the source and the detector being installed on one or more moving supports, the device being calibrated online (during operation of the device) in order to optimize the measurement results.

Figure 1:
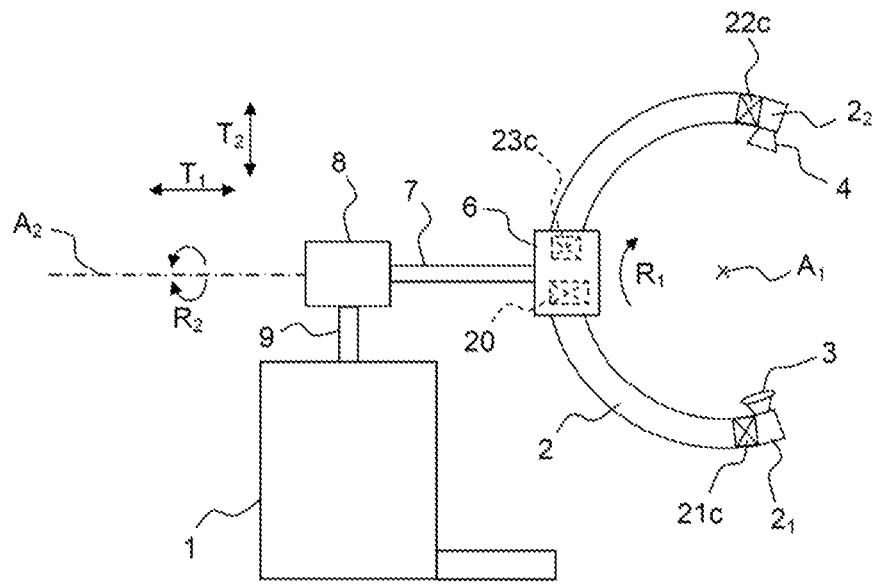
FIG. 1 shows a schematic depiction of an imaging apparatus of C-arm type.

In FIG. 1, the device D that is shown comprises a base 1 on which a C-arm 2 is installed. The C-arm supports a radiation source 3 consisting for example of an X-ray tube at a first end $2_1$ and an X-ray detector 4 that supplies a 2D image at a second end $2_2$. The C-arm is positioned in a hollow arc-shaped slide rail 6 in which it slides in an 'orbital' rotational movement R1, the axis A1 of which is the centre of a circle represented partly by the C-arm. The slide rail is attached to the base 1 via a holding component 8 and an arm 7 for providing a second 'angular' rotational movement R2 along a second axis A2.

To calibrate the apparatus online, the device comprises a first sensor, such as an inertial sensor 21c, positioned close to the source 3 and at least one second sensor, such as an inertial sensor 22c, positioned close to the detector 4. The two inertial sensors 21c, 22c are configured to perform acceleration and speed measurements that will allow a position Ps of the source and a position Pd of the detector to be deduced therefrom using principles known to those skilled in the art.

The sensor configured to perform acceleration and speed measurements may be an inertial sensor, an ultrasound sensor, an optical sensor, an encoder or any other device known to those skilled in the art and that provides the measurement function on the basis of which it is possible to calculate or estimate positions.

The device may also comprise an encoder sensor 20 configured to measure the angular position Pa of the orbital movement of the C-arm at a given time t. The use of an encoder allows simpler and more reliable measurement. Some types of sensor will be given by way of example further on in the description.

To perform the measurements, the device is linked to a driving and data processing module 10 (FIG. 2) comprising the following elements: a synchronization module 23 for synchronously triggering measurements at the sensors fitted on the arm, a processor 24 executing the steps of the method according to the invention, and a module 25 for pre-processing the measurements performed by the sensors.

The synchronization module 23 makes it possible to simultaneously timestamp the image acquisitions and the measurements of the inertial sensors and of the encoder fitted on the arm. The measurement results (inertial sensors and arm) take the form for example of a table or of a database containing, for a given time ti, a 2D image acquisition and three measurements.

Figure 2:
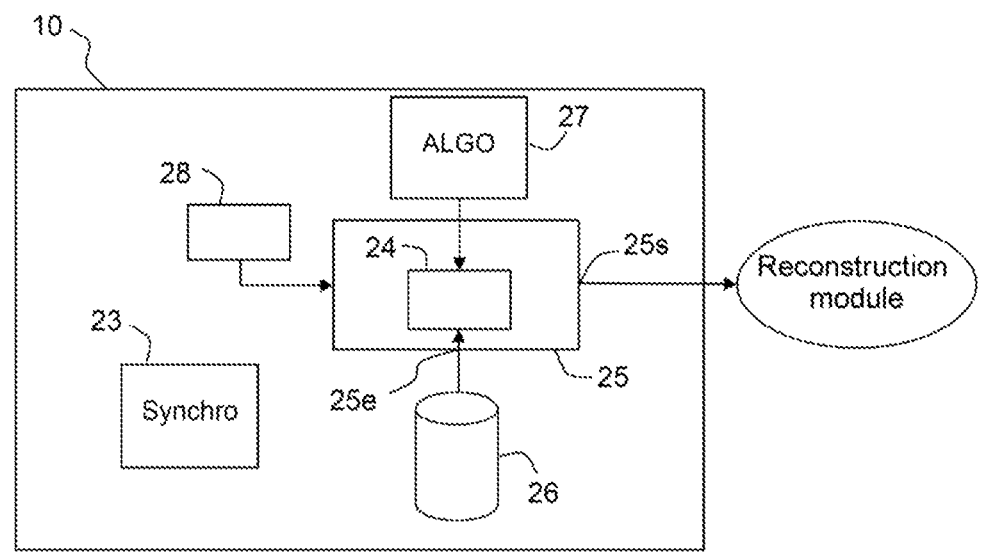
FIG. 2 shows a diagram of a data processing module.

According to FIG. 2, the pre-processing module comprises an input 25e receiving a dynamic operating model 26 of the apparatus and a data merging algorithm 27, for example of Kalman type or of extended Kalman type, taking into account at least the three measurements, of the two inertial sensors and of the encoder, 28, and the dynamic operating model of the apparatus 26 in order to deduce therefrom a projection matrix that will be transmitted, via an output 25s of the pre-processing module, to a reconstruction module.

The number of encoders that are used is chosen for example depending on the number of degrees of freedom (rotation-translation) of the apparatus. The role of the encoders is notably to determine, with low accuracy but in a stable manner, the absolute position of the apparatus with respect to a reference point linked to the base of the apparatus (coordinates of the C-arm apparatus at which the wheels are attached or reference point for example), and thus to ascertain a first approximation of the intrinsic and extrinsic parameters or else the associated 4×3 3D/2D projection matrix that will be used according to techniques known to those skilled in the art to reconstruct a 3D image.

To determine the position of the C-arm, use will be made for example of a linear potentiometric positioning rule for the 'orbital' movement R1, an encoder with an optical encoder wheel for the 'angular' movement R2 and two rectilinear movements for the movements T1 ('forwards/backwards') and T2 ('up/down'), FIG. 1.

To displace the arm, the latter may be equipped with a flexible toothed belt and the slide rail 6, supporting the arm, with a notched wheel that entrains the flexible belt.

Figure 3:
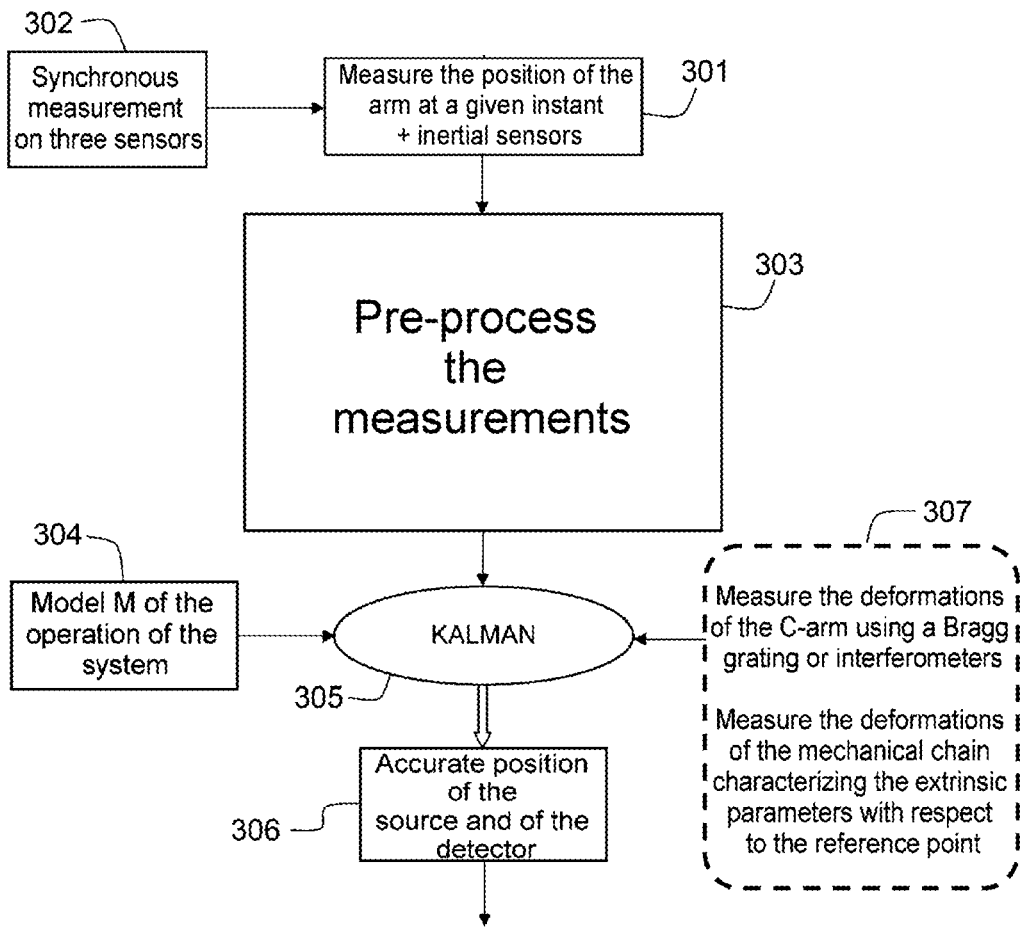
FIG. 3 shows an overview of the steps implemented in the calibration according to the invention.

FIG. 3 shows a flow chart listing the sequence of the steps implemented by the method.

In the following example, the method uses for example the encoder 20 to note the position of the C-arm and at least the two inertial sensors positioned at each of the ends of the arm, where the source and the detector are located. The measurements are performed 301 synchronously 302 by virtue of the synchronization module, which transmits an order to trigger the measurements simultaneously to the encoder and the two inertial sensors. The measurements of the inertial sensors (acceleration and angular speed) are recorded and pre-processed. The pre-processing involves for example filtering these measurements, extracting a bias value and sampling the measurements again. The processor will also establish a dynamic model M of the operation of the device D, using principles known to those skilled in the art, or else a dynamic operating model will be stored in a database and sent to the processor.

The two measurements performed by the two inertial sensors 21c, 22c, and the measurement Pa performed by the encoder, are transmitted 303 to the data pre-processing module 25. In this example, an extended Kalman filter is used. It is also possible to use a filter having an equivalent function. The extended Kalman filter, 305, receives at input the dynamic model M of the operation of the apparatus, 304, and the three measurements Ps, Pd and Pa from the data processing module. The data merging step performed by the extended Kalman filter makes it possible notably to estimate the pose (direction and orientation) of the detector and of the source, as well the error made in this estimation. On the basis of the merging of these data, the extended Kalman filter estimates a position of the X-ray source and an accurate position of the detector, 306. The accuracy of the positions that are obtained will be for example contained within the interval [100 µm-500 µm]. The 3D/2D projection matrix will then be calculated on the basis of the accurate positions.

The accuracy results notably from the fact that the system according to the invention is non-causal, with the estimation not taking place in real time, thereby making it possible to use 'backward-forward' filters.

A dynamic operating model M of the device may be constructed. In spite of the non-reproducibility of the movement of the C-arm, the difference between two courses remains limited. An average path of the C-arm may be established and integrated into the model. Accurate models of the sensors used (inertial model) are established and integrated into the observation models of the extended Kalman filter.

It is also possible to use heterogeneous sensors (inertial sensors or of the same type) in order to exploit the redundancy of the pose information and allow better smoothing of uncorrelated errors.

To increase the accuracy in the position that is obtained, the device may be equipped with a network of inertial sensors of MEMS type with six or nine degrees of freedom and situated at chosen positions. Due to their low cost and ease of implementation, the number of inertial sensors may be high.

For example, one solution consists in positioning inertial sensors as follows:
- a first reference inertial sensor linked to the system reference point,
- an inertial sensor on the point of rotation of the C-arm (at the mechanical coupling for making the orbital movement),
- an inertial sensor on the centre point of the C-arm, or distributed over the entire length of the arm,
- three or four inertial sensors at the detector and the X-ray source that are attached to the two ends of the C-arm.

The sensor 22c is for example an inertial sensor with at least six degrees of freedom: three accelerometers and three gyrometers, and the sensor 21c is an inertial sensor with at least three degrees of freedom: three accelerometers.

In FIG. 1, a third inertial sensor 23c is positioned midway between the two inertial sensors 21c, 22c.

According to one variant embodiment, as described hereinafter, the Kalman filter may also receive additional measurements (FIG. 3, 307), such as measurements of the deformations of the C-arm, which are obtained using one or more Bragg gratings, not shown for the sake of simplicity. These gratings may be positioned along the C-arm on the faces or the edges in order to measure the deformation of the arm.

Another solution for increasing accuracy involves using one or more Mach Zehnder or Michelson interferometers. These will allow measurement via one or more flexible rods that are for example non-extendable, non-compressible and situated in a sheath arranged along the C-arm.

By merging all of the data: measurement data obtained by the inertial sensors, the encoders, the Bragg gratings and the interferometers, all of the parameters are able to be obtained with better accuracy. The measurements of the encoders make it possible notably to reinforce the measurements of the inertial sensors.

To reduce the number of electronic sensors for measuring the deformation in all directions in space, one variant provides for merging the data of all of the sensors with the results of the modelling of the mechanical deformations of the C-arm. Specifically, depending on the design of the C-arm, it may be the case that it is enough to measure only a small number of deformations while still retaining sufficient accuracy of the estimation.

According to one variant embodiment, the combination of one or more laser telemeters will allow measurement with greater accuracy, for example of the order of a micron, of the differences in the three dimensions of the displacement of the C-arm with respect to the mechanism for rotating the C-arm on the orbital movement with respect to its theoretical path. One variant is that of using a laser scanning system that measures, in real time, part of the profile of the C-arm.

Another solution, in place of the optical measurement solutions (interferometer, laser telemeters, etc.), is that of using a combination of an RFID sensor combined with ultrasound sensors in order to measure the same differences; these solutions based on relative 'time-of-flight' measurements are not as accurate as optical measurements but are also less expensive and therefore better suited to the final system that is targeted.

A triangulation operation on the basis of the measurements will then make it possible to measure the displacements of the mechanical part holding the C-arm and allowing its orbital rotation with respect to the reference point linked to the reference point of the apparatus. This movement combines 'backwards/forwards' and 'up/down' displacements. Any other accurate tracking system may be used for this additional measurement, for example an optical system, a 2D or 3D laser scanning system, etc.

The extrinsic parameters, as they have been defined, relate to a reference point linked to the frame of the apparatus, and not to the table on which the patient is located. The transformation between the two reference points may be performed without difficulty by those skilled in the art.

The invention makes it possible to calibrate the device online, in real time, so has to have, at any time, the position of the source and of the detector in a precise manner. It provides the option of determining the intrinsic and extrinsic geometric parameters of a C-arm online in order to accurately deduce therefrom the 3D/2D projection matrix that allows the creation of high-quality 3D tomographic constructions of a patient, but also accurate positioning of the C-arm during a surgical operation.

The invention claimed is:

1. A system for calibrating a device D comprising at least one X-ray radiation source and a detector, the X-ray radiation source and the detector being installed on at least one moving support, the moving support being linked to a base via at least one axis of rotation, comprising at least the following elements:
   at least one first sensor positioned close to the X-ray radiation source and at least one second sensor positioned close to the detector, the two first and second sensors being configured to estimate through calculation a position Ps of the source and a position Pd of the detector by merging the position measurements in order to calibrate the system online and without the need for calibration offline a priori, and a sensor for sensing the angular position of the moving support,
   a synchronization module configured to synchronously trigger the measurements of the sensors,
   a module for pre-processing the measurements of the sensors, said processing module comprising an input receiving an operating model M of the device and a data merging algorithm taking into account at least the two measurements of the sensors and the model M in order to estimate an accurate position value for the source Ps and for the detector Pd.

2. The system according to claim 1, wherein said measurement sensors are inertial sensors.

3. The system according to claim 2, wherein said inertial sensors are distributed along the moving support between the X-ray radiation source and the detector.

4. The system according to claim 3, wherein it comprises at least three inertial sensors, two of the inertial sensors being positioned at each end of the moving support and the third sensor midway between the two ends.

5. The system according to claim 1, wherein the moving support is an arm and in that it comprises an encoder configured to measure an angular position Pa of the movement of the arm.

6. The system according to claim 1, wherein the moving support is an arm and in that it comprises N encoders, with N being greater than or equal to 1, the number N being equal to the number of degrees of freedom of the system.

7. The system according to claim 1, wherein the data merging algorithm is a Kalman algorithm or an extended Kalman algorithm.

8. The system according to claim 1, wherein the moving support is a C-arm.

9. A method for online calibration of a device D comprising at least one X-ray radiation source and a detector that are associated with at least one moving support, comprising at least the following steps:
   simultaneously recording measurements performed by at least one sensor close to the X-ray radiation source and a sensor close to the detector and a sensor configured to measure the angular position of the moving support,
   transmitting these measurements, as well as an operating model M of the device D, to a module configured to merge data of the measurements in order to estimate a position value Pd for the detector and Ps for the source, as well as a measurement error, without the need for calibration offline a priori.

10. The method according to claim 9, wherein a Kalman filter or an extended Kalman filter is used to merge all of the data.

11. The method according to claim 9, wherein inertial sensors are used to perform measurements.

12. The method according to claim 9, wherein the measurements given by the sensors close to the source and to the end are merged with the measurement of N encoders, with N being greater than or equal to 1, the number N being equal to the number of degrees of freedom of the system.

13. The method according to claim 9, wherein an opto-electronic sensor is used to additionally measure mechanical deformations of the moving support.

14. The method according to claim 9, wherein one or more Bragg gratings or interferometers are used to determine deformation of the moving support.

15. The method according to claim 9, wherein to measure the mechanical deformation of the moving support, a device chosen from the following list is used: one or more interferometers and laser telemeters, one or more RFID/ultrasound sensors.

* * * * *